United States Patent
Fenwick et al.

(10) Patent No.: US 6,781,027 B2
(45) Date of Patent: Aug. 24, 2004

(54) MIXED DENIER FLUID MANAGEMENT LAYERS

(75) Inventors: Christopher Dale Fenwick, Alpharetta, GA (US); Roland Columbus Smith, Jr., Gainesville, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 195 days.

(21) Appl. No.: 10/022,863

(22) Filed: Dec. 14, 2001

(65) Prior Publication Data

US 2003/0130634 A1 Jul. 10, 2003

(51) Int. Cl.$^7$ .............................................. A61F 13/15
(52) U.S. Cl. ...................... 604/365; 604/367; 604/370; 604/372; 428/213; 442/361; 442/362; 442/363; 442/364
(58) Field of Search .................. 604/365, 367, 604/370, 372; 428/212, 213, 219; 442/334, 340, 344, 346, 361–364, 392

(56) References Cited

U.S. PATENT DOCUMENTS

| | | | |
|---|---|---|---|
| 3,802,817 A | 4/1974 | Matsuki et al. ................ | 425/66 |
| 3,855,046 A | 12/1974 | Hansen et al. ............... | 161/150 |
| 4,142,016 A | 2/1979 | Perry .......................... | 428/284 |
| 4,162,344 A | 7/1979 | Rones ......................... | 428/212 |
| 4,216,772 A | 8/1980 | Tsuchiya et al. | |
| 4,307,721 A | 12/1981 | Tsuchiya et al. ....... | 128/290 W |
| 4,340,563 A | 7/1982 | Appel et al. ................. | 264/518 |
| 4,364,992 A | 12/1982 | Ito et al. | |
| 4,377,615 A | 3/1983 | Suzuki et al. ............... | 428/213 |
| 4,477,516 A | 10/1984 | Sugihara et al. | |
| 4,537,822 A | 8/1985 | Nanri et al. ................. | 428/212 |
| 4,640,810 A | 2/1987 | Laursen et al. .............. | 264/518 |
| 4,652,484 A | 3/1987 | Shiba et al. | |
| 4,704,112 A | 11/1987 | Suzuki et al. ............... | 604/378 |
| 4,794,034 A | 12/1988 | Nishizawa et al. .......... | 428/218 |
| 4,798,603 A | 1/1989 | Meyer et al. ................ | 604/378 |
| 4,883,707 A | 11/1989 | Newkirk ...................... | 428/219 |
| 5,037,409 A | 8/1991 | Chen et al. .................. | 604/358 |
| 5,257,982 A | 11/1993 | Cohen et al. ................ | 604/378 |
| 5,271,780 A | 12/1993 | Baigas, Jr. | |
| 5,277,976 A | 1/1994 | Hogle et al. ................. | 428/397 |
| 5,298,315 A | 3/1994 | Fukui et al. ................. | 428/298 |
| 5,330,457 A | 7/1994 | Cohen .......................... | 604/378 |
| 5,334,177 A | 8/1994 | Cohen .......................... | 604/378 |
| 5,366,453 A * | 11/1994 | Zehner et al. .......... | 604/385.29 |
| 5,418,045 A | 5/1995 | Pike et al. ................... | 428/198 |
| 5,437,653 A | 8/1995 | Gilman et al. ............... | 604/378 |
| 5,470,326 A | 11/1995 | Dabi et al. ................... | 604/383 |
| 5,492,751 A | 2/1996 | Butt, Sr. et al. ............ | 428/198 |
| 5,505,719 A | 4/1996 | Cohen et al. ................ | 604/372 |
| 5,531,727 A | 7/1996 | Cohen et al. ................ | 604/378 |
| 5,569,226 A | 10/1996 | Cohen et al. ................ | 604/378 |
| 5,683,809 A | 11/1997 | Freeman et al. | |
| 5,700,254 A | 12/1997 | McDowall et al. ......... | 604/378 |
| 5,728,081 A | 3/1998 | Baer et al. ................... | 604/370 |
| 5,733,635 A | 3/1998 | Terakawa et al. ........... | 428/198 |
| 5,752,945 A | 5/1998 | Mosley et al. .............. | 604/370 |
| 5,817,394 A | 10/1998 | Alikhan et al. ............. | 428/137 |
| 5,820,615 A | 10/1998 | Koczab ....................... | 604/378 |
| 5,843,064 A | 12/1998 | Koczab ....................... | 604/378 |
| 5,853,628 A | 12/1998 | Varona .......................... | 264/6 |
| 5,876,388 A | 3/1999 | McDowall et al. ......... | 604/384 |
| 5,885,267 A | 3/1999 | Mishima et al. ............ | 604/378 |
| 5,885,516 A | 3/1999 | Christensen ................. | 264/518 |
| 5,913,851 A * | 6/1999 | Gryskiewicz et al. .. | 604/385.31 |
| 5,989,688 A | 11/1999 | Barge et al. ................. | 428/198 |
| 6,087,551 A | 7/2000 | Pereira | |
| 6,103,954 A | 8/2000 | Grondin et al. ............. | 604/370 |
| 6,592,561 B2 * | 7/2003 | Simard et al. .......... | 604/385.04 |

FOREIGN PATENT DOCUMENTS

| | | | |
|---|---|---|---|
| EP | 0 875 615 | 11/1998 | |
| GB | 2 272 859 | 6/1994 | |
| JP | 08-164160 A2 | 6/1996 | |
| JP | 2846448 B2 | 1/1999 | |
| WO | 96/11107 | 4/1996 | ............ B32B/5/26 |
| WO | 98/24621 | 6/1998 | ............ B32B/5/26 |
| WO | 99/32061 | 7/1999 | ........... A61F/13/20 |
| WO | 00/37723 | 6/2000 | |
| WO | 00/49215 | 8/2000 | |
| WO | 00/74620 | 12/2000 | ............ B27N/3/00 |
| WO | 01/00917 | 1/2001 | |

* cited by examiner

Primary Examiner—John J. Calvert
Assistant Examiner—Jacqueline F Stephens
(74) Attorney, Agent, or Firm—Nathan P. Hendon

(57) ABSTRACT

A nonwoven surge material for personal care products, which is a nonwoven fabric made of a homogeneous blend of large and small denier fibers. The small or first denier fiber preferably has an average denier less than 2, is at least 3 denier less than the second or larger fiber and the large or second denier fiber has an average denier between 4 and 15. The nonwoven fabric is a mixture of these fibers in amounts of from 25 to 75 weight percent of each type of fiber. The fabric may have a basis weight between 30 and 200 gsm. The first denier fiber may be a bicomponent fiber which may be a sheath/core polyethylene/polypropylene bicomponent fiber. The second denier fiber may be made from a polyester. It is also possible that the fibers have a hydrophilic treatment added to their surface to increase their hydrophilicity.

20 Claims, No Drawings

MIXED DENIER FLUID MANAGEMENT LAYERS

BACKGROUND OF THE INVENTION

The present invention concerns formed materials mainly for personal care products like diapers, training pants, swim wear, absorbent underpants, adult incontinence products and feminine hygiene products. This material may also be useful for other applications such as, for example, in bandages and wound dressings, nursing pads and in veterinary and mortuary applications.

Personal care articles usually have multiple layers of material of some sort to absorb liquids from the body. These layers may include natural fibers, synthetic fibers and superabsorbent particles in varying proportions. When liquid such as urine is deposited into a personal care product like a diaper, it goes through the uppermost layers, typically a liner against the body and a "surge" or "intake" layer designed to provide temporary liquid holding capacity. The product may also have a "distribution" layer designed to move liquid in the X and Y directions in order to utilize more of the absorbent core. After going through these upper layers, the urine enters the absorbent core portion of the product. The absorbent core permanently retains the liquid.

Various approaches have been used in the past to hold liquid, yet still allow it to be transferred eventually to another layer like the core. Similarly, intake materials have been investigated which take in liquid with varying degrees of success. There remains a need in the art for a fabric for use in personal care products with improved fluid handling capabilities. Such a material will intake and retain fluid more efficiently than has been practiced in the past.

SUMMARY OF THE INVENTION

In response to the discussed difficulties and problems encountered in the prior art, a new structural composite comprising a nonwoven fabric made of a homogeneous blend of large and small denier synthetic fibers has been developed. The nonwoven material is for personal care products and is made from a mixture of fibers of different denier, where a first denier fiber has an average denier at least 3 denier less than a second fiber and the second fiber has an average denier between 4 and 15, and where the material has a basis weight between 30 and 200 gsm. The first denier fiber has an average denier of 2 or less and the second denier fiber preferably has an average denier between 6 and 15.

The nonwoven material can have the first denier fiber present in an amount between 25 and 75 weight percent and the second denier fiber present in an amount between 75 and 25 weight percent. More particularly the first denier fiber can be present in an amount between 40 and 60 weight percent and the second denier fiber can be present in an amount between 60 and 40 weight percent. Still more particularly, the first denier fiber can be present in an amount of about 60 weight percent and the second denier fiber can be present in an amount of about 40 weight percent.

The first denier fiber may be a bicomponent fiber and may be a sheath/core bicomponent fiber selected of the group consisting of polyethylene/polypropylene, polyethylene/polyethylene terephalate and co-polyethylene terephalatel polyethylene terephalate bicomponent fibers. The second denier fiber may be made from a polyester. The fibers may have a hydrophilic treatment added to their surface.

The material made from the homogeneous blend of mixed denier fibers may be used as a surge material in personal care products. When used as a surge material in personal care products the material is capable of taking in fluid at a rate of 12 to 20 cc/sec. When used as a surge material in conjunction with a standard liner the structure is capable of up to an 8, 15 or even 20 percent TEWL improvement, when compared to a large fiber denier surge using the same standard liner.

Particular embodiments include a surge material for personal care products having between 40 and 60 weight percent of a first fiber having a first average denier and between 60 and 40 weight percent of a second fiber having a second average denier, where the first average denier is at least 3 denier less than the second average denier, the second average denier is between 4 and 15, and where the material has a basis weight between 30 and 200 gsm. Another embodiment is one in which the surge material for personal care products has about 60 weight percent of a first fiber in a bicomponent sheath/core configuration, made from polymers selected of the group consisting of polyethylene/polypropylene, polyethylenelpolyethylene terephalate and co-polyethylene terephalate/polyethylene terephalate and having a first average denier, and about 40 weight percent of a polyester second fiber having a second average denier, where the first average denier is at least 3 denier less than the second average denier, the second average denier is between 4 and 15, and where the material has a basis weight between 30 and 200 gsm. The small or first fiber has a average denier less than the large average denier fiber and the large or second denier fiber has a average denier between 4 and 15.

These materials are suitable for use in personal care products like diapers, training pants, incontinence products, bandages, and sanitary napkins.

Definitions

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

"Hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than to 90° are designated "nonwettable" or hydrophobic.

"Spunbonded fibers" refers to small diameter fibers that are formed by extruding molten thermoplastic material as filaments from a plurality of fine capillaries of a spinneret. Such a process is disclosed in, for example, U.S. Pat. No. 4,340,563 to Appel et al. and U.S. Pat. No. 3,802,817 to Matsuki et al. The fibers may also have shapes such as those described, for example, in U.S. Pat. No. 5,277,976 to Hogle et al. which describes fibers with unconventional shapes.

"Bonded carded web" refers to webs that are made from staple fibers which are sent through a combing or carding unit, which separates or breaks apart and aligns the staple fibers in the machine direction to form a generally machine direction-oriented fibrous nonwoven web. This material may be bonded together by methods that include point bonding, through air bonding, ultrasonic bonding, adhesive bonding, etc.

"Airlaying" is a well-known process by which a fibrous nonwoven layer can be formed. In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another using, for example, hot air to activate a binder component or a latex adhesive. Airlaying is taught in, for example, U.S. Pat. No. 4,640,810 to Laursen et al., and U.S. Pat. No. 5,885,516 to Christensen.

As used herein "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 19% bond area. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

As used herein, through-air bonding or "TAB" means a process of bonding a nonwoven bicomponent fiber web in which hot air is forced through the web. The temperature of the air is sufficient to melt one of the polymers of which the fibers are made. The air velocity is usually between 100 and 500 feet per minute and the dwell time may be as long as 6 seconds. The melting and resolidification of the polymer provides bonding. Through-air bonding (TAB) requires the melting of at least one component to accomplish bonding, so it is usually restricted to webs with two components like conjugate fibers or those which include an adhesive. In the through-air bonder, air having a temperature above the melting temperature of one component and below the melting temperature of another component is directed from a surrounding hood, through the web, and into a perforated drum supporting the web. Alternatively, the through-air bonder may be a flat arrangement wherein the air is directed vertically downward onto the web. The operating conditions of the two configurations are similar, the primary difference being the geometry of the web during bonding. The hot air melts the lower melting polymer component and thereby forms bonds between the filaments to integrate the web.

"Personal care product" means diapers, training pants, swim wear, absorbent underpants, adult incontinence products, bandages and feminine hygiene products. It further encompasses veterinary and mortuary products.

Test Methods and Materials

Basis Weight: A circular sample of 3 inches (7.6 cm) diameter is cut and weighed using a balance. Weight is recorded in grams. The weight is divided by the sample area. Five samples are measured and averaged.

Material caliper (thickness): The caliper of a material is a measure of thickness and is measured at 0.05 psi (3.5 g/cm$^2$) with a STARRET® bulk tester, in units of millimeters. Samples are cut into 4 inch by 4 inch (10.2 cm by 10.2 cm) squares and five samples are tested and the results averaged.

Density: The density of the materials is calculated by dividing the weight per unit area of a sample in grams per square meter (gsm) by the material caliper in millimeters (mm). The caliper should be measured at 0.05 psi (3.5 g/cm$^2$) as mentioned above. The result is multiplied by 0.001 to convert the value to grams per cubic centimeter (g/cc). A total of five samples would be evaluated and averaged for the density values.

FIFE: The horizontal Fluid Intake and Flowback Evaluation (FIFE) was performed on all samples to determine the intake potential of the composites. The FIFE entails insulting the structure by pouring a defined amount of 0.9 percent saline solution into a cylindrical column resting vertically on top of the structure and recording the time it takes for the fluid to be taken in by the structure. The sample to be tested is placed on a flat surface and the FIFE testing apparatus placed on top of the sample. The FIFE testing apparatus consisted of a rectangular, 35.43 by 20.3 cm, plexiglas flat piece upon which was centered a cylinder with an inside diameter of 30 mm. The flat piece had a 38 mm hole corresponding with the cylinder so that fluid could pass through it from the cylinder to the sample. The FIFE testing apparatus weighed 0.52 kg (1.14 pounds).

Intake times are typically recorded in seconds. Samples were cut into 2.5 by 7 inch (6.35 by 17.8 cm) pledgets and were inserted into a HUGGIES® step 4 diaper as a surge. The samples were then insulted three times at 100 mL per insult with a wait of 15 minutes between the time the fluid was completely absorbed and the next insult.

After the third insult, the materials were placed on a vacuum box under 0.5 psi of pressure with a piece of blotter paper on top. The blotter paper was 110 lb. Verigood paper made by Fort James Corporation and was 3.5 by 12 inches (8.9 by 30.5 cm). The blotter paper was weighed before and after the test and the resulting differential reported as the flowback value as grams of fluid desorbed.

Permeability: Permeability is obtained from a measurement of the resistance by the material to the flow of liquid. A liquid of known viscosity is forced through the material of a given thickness at a constant flow rate and the resistance to flow, measured as a pressure drop is monitored. Darcy's Law is used to determine permeability as follows:

$$\text{Permeability} = [\text{flow rate} \times \text{thickness} \times \text{viscosity} / \text{pressure drop}] \quad \text{[Equation 1]}$$

where the units are:

| permeability: | $cm^2$ or Darcy | 1 Darcy = $9.87 \times 10^{-9}$ $cm^2$ |
|---|---|---|
| flow rate: | cm/sec | |
| viscosity: | Pascal-sec | |
| pressure drop: | Pascals | |

The apparatus consists of an arrangement wherein a piston within a cylinder pushes liquid through the sample to be measured. The sample is clamped between two aluminum cylinders with the cylinders oriented vertically. Both cylinders have an outside diameter of 3.5 inches (8.9 cm), an inside diameter of 2.5 inches (6.35 cm) and a length of about 6 inches (15.2 cm). The 3 inch diameter web sample is held in place by its outer edges and hence is completely contained within the apparatus. The bottom cylinder has a piston that is capable of moving vertically within the cylinder at a constant velocity and is connected to a pressure transducer that is capable of monitoring the pressure encountered by a column of liquid supported by the piston. The transducer is positioned to travel with the piston such that there is no additional pressure measured until the liquid column contacts the sample and is pushed through it. At this point, the additional pressure measured is due to the resistance of the material to liquid flow through it. The piston is moved by a slide assembly that is driven by a stepper motor. The test starts by moving the piston at a constant velocity until the liquid is pushed through the sample. The piston is then halted and the baseline pressure is noted. This corrects for sample buoyancy effects. The movement is then resumed for a time adequate to measure the new pressure. The difference between the two pressures is the pressure due to the resistance of the material to liquid flow and is the pressure drop used in Equation (1). The velocity of the piston is the flow rate. Any liquid whose viscosity is known can be used, although a liquid that wets the material is preferred since this ensures that saturated flow is achieved. The measurements were carried out using a piston velocity of 20 cm/min, mineral oil (Peneteck Technical Mineral Oil manufactured by Penreco of Los Angeles, Calif.) of a viscosity of 6 centipoise.

TransEpidermal Water Loss (TEWL):

Skin hydration values are determined by measuring TransEpidermal Water Loss (TEWL) and can be determined by employing the following test procedure.

The test is conducted on adults on the forearm. Any medications should be reviewed to ensure they have no effect on test results and the subject's forearms should be free of any skin conditions such as rashes or abrasions. Subjects should relax in the test environment, which should be at about 72° F. (22° C.) with a humidity of about 40 percent, for about 15 minutes prior to testing and movement should be kept to a minimum during testing. Subjects should wear short sleeve shirts, not bathe or shower for about 2 hours before testing, and should not apply any perfumes, lotions, powders, etc., to the forearm.

The measurements are taken with an evaporimeter, such as a DERMALAB® instrument distributed by Cortex Technology, Textilvaenget 1 9560 Hadsund Denmark.

A baseline reading should be taken on the subject's forearm and should be less than 10 $g/m^2/hr$. Each test measurement is taken over a period of two minutes with TEWL values taken once per second (a total of 120 TEWL values). The digital output from the Evaporimeter EP1 instrument gives the rate of evaporative water loss (TEWL) in $g/m^2/hr$.

The end of a dispensing tube is placed on the mid-forearm for carrying out the test. is The eye of the tube should be facing the target loading zone. A product to be tested is placed on the subject's forearm directly over the end of the tube. The product may vary depending upon the type of material to be tested or material availability so care should be taken to ensure that test results are comparable. A stretchable net such as that available from Zens Industrial Knit Products of Milwaukee, Wis., should be placed over the product to help to hold it in place.

Three equal loadings of 70 ml of physiologic saline available from VWR Scientific Products (800-932-5000) at about 95° F. (35° C.) are delivered to the product at an interval of 45 seconds at a rate of 300 mils/minute by a pump such as a MASTERFLEX® Digi-Static batch/dispense pump. After 60 minutes, the product is removed from the subject's forearm and Evaporimeter readings taken immediately on the skin where the product had been.

TransEpidermal Water Loss values are reported as the difference between the one hour and baseline values in $g/m^2/hr$.

Horizontal Wicking: This test measures how far liquid will move in a fabric when only one end of the fabric is immersed in the liquid and the fabric is horizontal. The fabric to be tested is prepared by cutting it into 1 inch (2.5 cm) by 8 inch (20.3 cm) strips in the machine direction. The sample is weighed and marked every 0.5 inch (13 mm) in the long dimension. The sample is placed on a 5 inch (12.7 cm) by 10 inch (25.4 cm) horizontal wire grid and slightly weighted so that it remains flat on the wire. A half inch of one end of the sample is submerged in a 0.5 inch deep by 0.5 inch wide by 5 inch long reservoir containing 10 ml of dyed 8.5 g/l saline solution. The end of the sample in the reservoir is held in place with a cylindrical glass stirring rod having a length of 1.5 inches (3.8 cm) and a diameter of $5/16$ inches (7.9 mm) which also is submerged in the saline solution. The sample is allowed to rest with one end submerged in the reservoir for 20 minutes and is then carefully pulled horizontally out of the reservoir, cut at each 0.5 inch mark and each section weighed.

The dry sample weight is subtracted from the wet sample weight to arrive at fluid grams, and the 0.5 inch submerged in the reservoir is not considered. The total distance wicked is recorded along with the total grams of fluid wicked.

DETAILED DESCRIPTION OF THE INVENTION

This invention concerns a nonwoven web having a blend of synthetic fibers of different diameters.

The non-woven fabrics of the present invention may be formed by conventional processes including spunbonding, airlaying and bonding and carding processes. In bonding and carding, and airlaying processes, the initial process step is to form a web of homogeneously mixed low and high denier fibers. Accordingly, bales of low denier staple fibers and high denier staple fibers are homogeneously mixed in an air mixing chamber and then either carded to form a carded web or randomly laid on a foraminous forming structure to form a fibrous web.

The mixed denier fibers must be stabilized in a consolidated form via some form of bonding. This may be done thermally, ultrasonically or preferably, through the use of through-air-bonding (TAB). Prior to bonding the fibers may be formed in such a way as to facilitate orientation in either the x, y or z direction. One preferred method of thermal bonding is through the use of a through air bonder (TAB). Post bonded material may be creped, to orient fibers out of the x-y plane, or they may remain in the x-y plane. Additional layers may be added to the material by thermal bonding, mechanical bonding and the like.

The material may additionally be creped after formation, given Z-direction fiber orientation during formation, or may be a relatively flat nonwoven structure.

Additional layers may be added to the structure and it may be included in personal care products. A liner layer may be placed above the surge of the invention, where the liner is intended to be in contact with the skin of a wearer and is made from small denier fibers (e.g. 2–3 denier). These fibers may be synthetic fibers as described above and may be, for example, a mixture of 2 denier bicomponent fibers and 3 denier PET fibers. Smaller fibers in the liner layer make this layer aesthetically pleasing and soft to the touch.

An additional layer may be placed below the surge of this invention also and may also be of low (2–3) denier fibers. Alternatively, the layer below the surge of this invention may be a relatively large denier (e.g. 5–7 denier) fiber web.

The mixed denier web is a homogeneous mixture of staple synthetic fibers where one of the fiber types is of a relatively small average denier and one is of a relatively larger average denier fiber, when compared to each other. The small denier fiber must have an average denier at least 3 less than the larger denier fiber and from a positive amount to less than or equal to 2, more particularly even less than 1, and the larger denier fiber should have an average denier between 4 and 15 and preferably between 6 and 15. The mixed denier web is a mixture of these fibers in amounts of from 25 to 75 weight percent of each type of fiber, or more particularly between 40 and 60 percent, or still more particularly the small denier fiber could be present in an amount of about 60 percent and the large denier fiber could be present in an amount of about 40 percent. The small denier fiber, for example, could be in an amount of 25 percent and the large denier fiber in an amount of 75 percent. Alternatively, the large denier fiber could be present in an amount of 25 percent and the small denier fiber present in an amount of 75 percent. These ratios as well as all ratios within this range are intended to be within the purview of the invention.

The fibers used to make the web of this invention are thermally bondable synthetic polymer fibers. Synthetic fibers include polymeric fibers like polyolefins, polyamides, polyesters, polyethers, polyethylene terephalate and combinations thereof in bicomponent form. Synthetic fibers may also include kosmotropes for product degradation. Its preferred that natural fibers like cotton and pulp not be included in the web of this invention, i.e., that the web be essentially free of natural fibers.

Bicomponent fibers are generally used as binders to help provide mechanical integrity and stabilization. Preferred fibers for inclusion are those having a low relative melting point such as polyolefin fibers. Lower melting point polymers provide the ability to bond the fabric together at fiber cross-over points upon the application of heat. In addition, fibers having a lower melting polymer, like conjugate and biconstituent fibers are suitable for practice of this invention. Fibers having a lower melting polymer are generally referred to as "fusible fibers". By "lower melting polymers" what is meant are those having a glass transition temperature less than about 175° C. It should be noted that the texture of the absorbent web can be modified from soft to stiff through selection of the fusion and quenching behavior of the polymer.

Exemplary binder fibers include conjugate fibers of polyolefins, polyamides and polyesters. Three suitable binder fibers are sheath/core conjugate fibers available from KoSa Inc. (Charlotte, N.C.) under the designation T-255 and T-256, both with a polyolefin sheath, or T-254, which has a low melt co-polyester sheath. Fibers with sheath/core compositions of polyethylene/polypropylene, polyethylenepolyethylene terephalate and co-polyethylene terephalate/polyethylene terephalate are particularly suited to the practice of this invention. Many other suitable binder fibers are known to those skilled in the art, and are available by many manufacturers such as Chisso and Fibervisions LLC of Wilmington, Del.

Treatments may be added to the synthetic fibers which are generally hydrophobic, in order to increase the fiber's hydrophilicity. These treatments are sometimes internal additives that "bloom" to the surface of the fiber upon formation, though are more commonly surface treatments added after formation. Topical treatments include the "L1" finish available from KoSa Inc. (Charlotte, N.C.) and the "HR6" finish from Chisso Corporation of Japan and are generally added at an amount of about 0.1 to 1 weight percent, more particularly about 0.5 weight percent. The L1 finish, for example, has sorbitan monooleate (SPAN 80), ethoxylated hydrogentated castor oil (EO25) and polyethylene glycol-400-monolaurate (POE9), all of which are fatty esters. Topical treatments may be applied by any method known in the art including spraying, dipping, and the like.

The mixed denier surge material of this invention may be produced at a target basis weight of 30 to 200 gsm, more particularly 50 to 150 gsm and still more particularly 80 to 110 gsm.

Absorbent articles usually have a fluid impermeable outer cover, backsheet or "baffle" facing the wearer's garments, an absorbent core, and a body side liner. The liner is usually a non-woven fabric, formed from an open but interconnected network of thermoplastic fibers. The body side liner is normally in contact with or faces the wearer of the absorbent article during use.

In accordance with the present invention, there is also provided a novel absorbent article, such as a sanitary napkin or diaper, having a fluid permeable cover sheet or liner, a fluid impermeable barrier sheet, an absorbent core between the liner and the backsheet. The liner may be a mixed denier nonwoven fabric formed from an interconnected network of synthetic polymer fibers. The fibers are the homogeneous blend of higher denier staple fibers and lower denier staple fibers as described above.

The liner is designed to be highly permeable to liquid and to be non-irritating to the skin. Such a liner allows urine and menses to penetrate through itself quite easily and feels soft to the skin. The liner may optionally have more than one layer or may have one layer in a central area with multiple layers in the side areas. The opposite configuration is also possible with two or more layers in the central area and only one on the sides. Such a liner may be advantageous for menstrual use or for delivery of medicaments, because of its high fibrous surface area.

Liners may also incorporate treatments of lotions or medicaments to improve the environment near the skin or to actually improve skin health. Such treatments include aloe, vitamin E, baking soda and other preparations as may be known or developed by those skilled in the art.

The outer cover or "baffle" is designed to be impermeable to liquid in order to keep the clothing or bedding of the wearer from becoming soiled. The impermeable baffle is preferably made from a thin film and is generally made from plastic though other materials may be used. Nonwoven webs, films or film coated nonwovens may be used as the baffle as well. Suitable film compositions for the baffle include polyethylene film which may have an initial thickness of from about 0.5 mil (0.012 millimeter) to about 5.0 mil (0.12 millimeter). The baffle may optionally be composed of a vapor or gas permeable, microporous "breathable" material, that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability. Other suitable thermoplastic materials like other olefins, nylons, polyesters or copolymers of, for example, polyethylene and polypropylene may also be used.

The core portion of a personal care product is designed to absorb liquids and secondarily to contain solids. The core, known also as an absorbent core, a retention layer, and the like, may be made with pulp and/or superabsorbent materials. These materials absorb liquids quite quickly and efficiently in order to minimize leakage. Core materials may be made according to a number of processes including the coform process, airlaying, and bonding and carding and should be between 50 and 200 gsm.

Various other layers may be included in some personal care products. These include surge layers, usually placed between the liner and core and designed, as the name suggests, to contain large surges of liquid so that the core may absorb it over time. The homogeneous blend of mixed denier fibers may be used as a surge layer as well. Distribution layers also are included in many personal care products. Distribution layers are usually located next to the core and accept liquid from the surge or liner layer and distribute it to other areas of the core. In this manner, rather than absorbing liquid exclusively in the vicinity of the target area, more of the absorbent core is used.

Examples of nonwoven webs according to the invention are provided below.

EXAMPLE 1

A mixed denier surge material of this invention is a homogeneous mixture of 60 weight percent bicomponent staple fiber and 40 weight percent polyester staple fiber. The bicomponent fiber is a 0.9 denier polyethylene/polypropylene (PE/PP), sheath/core fiber, with an HR6 finish applied topically at 0.5 weight percent, from Chisso Corporation of Japan. A suitable polyester fiber is supplied by Kosa and is a 6 denier PET fiber with an L1 finish applied topically. These fibers were processed using a conventional bonding and carding process followed by through-air-bonding, to produce a nonwoven web having a basis weight of about 90 gsm and a bulk of about 0.09 inches (2.29 mm).

EXAMPLE 2

A mixed denier surge material of this invention is a homogeneous mixture of 40 weight percent bicomponent staple fiber and 60 weight percent polyester staple fiber of the same fibers as in Example 1, made into a nonwoven web in the same manner.

Control 1: This Control (not an example of the invention) was a nonwoven web made from fibers having the same denier. The fibers were 60 weight percent 2 denier PE/PET, sheath/core fiber, with an L1 finish applied topically at 0.5 weight percent and 40 weight percent of 3 denier PET fiber with an L1 finish applied topically. These fibers were processed into a nonwoven fabric using a conventional bonding and carding process followed by through-air-bonding, to produce a web with a basis weight of about 90 gsm and a bulk of 0.06 inches.

Control 2: This Control (not an example of the invention) was a nonwoven web made from fibers which were 60 weight percent 3 denier PE/PP, sheath/core fiber, with an HR6 finish applied topically at 0.5 weight percent and 40 weight percent of 6 denier PET fiber with an L1 finish applied topically. These fibers were processed into a nonwoven fabric using a conventional bonding and carding process followed by through-air-bonding, to produce a web with a basis weight of about 90 gsm and a bulk of 0.14 inches (3.56 mm).

The Control and the Examples were tested according to the horizontal wicking, permeability and FIFE tests given above and the test results reported in Table 1.

TABLE 1

| Sample | Horizontal (in) | Wicking (grams) | Permeability (darcies) | Sat Cap Load (g/g) | Total Cap. Load (g) | FIFE (sec) 1st | 2nd | 3rd | Flowback (g) |
|---|---|---|---|---|---|---|---|---|---|
| Example 1 | 8.0 | 5.7 | 1758 | 22.8 | 19.0 | 13.0 | 19.7 | 14.0 | 15.4 |
| Example 2 | 2.0 | 2.0 | 3450 | 22.8 | 19.7 | 11.7 | 13.3 | 11.7 | 14.9 |
| Control 1 | 8.0 | 4.2 | 1796 | 14.5 | 16.0 | 12.9 | 14.5 | 16.8 | 19.4 |
| Control 2 | 1.5 | 1.7 | 4900 | 16.7 | 20.0 | 8.7 | 9.4 | 9.7 | 11.7 |

As can be seen from the results in Table 1, the Examples 1 and 2 of the invention had much better balance of fluid intake and fluid handling than the two controls. Due to the difference in fiber size (0.9 and 6 dpf), fluid intake times and fluid wicking distances fell between those of Control 1 and Control 2. In addition the FIFE testing third insult results indicate sustained intake over multiple insults as well as how consistent the structure is maintained for fluid intake.

Example 1 and Control 1 were also placed beneath a polypropylene liner and tested according to the TEWL test given above. The TEWL for the Example 1 was 14.82 and that of the Control 1 was 16.08. The Example 1 thus had a TEWL about 8 percent less than that of the Control 1, which did not have deniers within the requirements of the invention.

Example 1 and Control 2 were also placed beneath a standard liner and tested according to the TEWL test given above. The standard liner was a polypropylene spunbond liner with 2.8 dpf fibers, treated topically with Achovel-Glucopon at 0.3 weight percent. The TEWL for the Example 1 was 14.82 and that of Control 2 was 21.45. The Example 1 thus had a TEWL about 30 percent less than that of Control 2. It is believed that the mixed denier surge allows for rapid intake as the Controls do, but also provides higher capillarity regions that help to facilitate removal of fluid from the liner.

As will be appreciated by those skilled in the art, changes and variations to the invention are considered to be within the ability of those skilled in the art. Examples of such changes and variations are contained in the patents identified above, each of which is incorporated herein by reference in its entirety to the extent consistent with this specification. Such changes and variations are intended by the inventors to be within the scope of the invention.

What is claimed is:

1. A nonwoven material for personal care products comprising a mixture of synthetic fibers of different denier, wherein a first denier fiber is a bicomponent fiber and has an average denier of 1 or less, said first fiber has an average denier at least 3 denier less than a second fiber, and said second fiber has an average denier between 4 and 15, and wherein said material has a basis weight between 30 and 200 gsm.

2. The nonwoven material of claim 1 wherein said second denier fiber has a denier between 6 and 15.

3. The nonwoven material of claim 1 wherein said first denier fiber is present in an amount between 25 and 75 weight percent and said second denier fiber is present in an amount between 75 and 25 weight percent.

4. The nonwoven material of claim 1 wherein said first denier fiber is present in an amount between 40 and 60 weight percent and said second denier fiber is present in an amount between 60 and 40 weight percent.

5. The nonwoven material of claim 1 wherein said first denier fiber is present in an amount of about 60 weight percent and said second denier fiber is present in an amount of about 40 weight percent.

6. A sanitary napkin comprising the material of claim 1.

7. The nonwoven material of claim 1 wherein said first denier fiber is a sheath/core bicomponent fiber selected of the group consisting of polyethylene/polypropylene, polyethylene/polyethylene terephalate and co-polyethylene terephalate/polyethylene terephalate bicomponent fibers.

8. The nonwoven material of claim 1 wherein said second denier fiber is made from a polyester.

9. The nonwoven material of claim 1 wherein said fibers have a hydrophilic treatment added to the surface of said fibers.

10. A surge material comprising the nonwoven web of claim 1 and providing an improvement in TEWL of at least 8 percent.

11. A surge material comprising the nonwoven web of claim 1 and providing an improvement in TEWL of at least 15 percent.

12. A surge material comprising the nonwoven web of claim 1 having an intake rate of at least 12 cc/sec.

13. A diaper comprising the material of claim 1.

14. A training pant comprising the material of claim 1.

15. An incontinence product comprising the material of claim 1.

16. A bandage comprising the material of claim 1.

17. A surge material for personal care products comprising about 60 weight percent of a first fiber in a bicomponent sheath/core configuration, made from polymers selected of the group consisting of polyethylene/polypropylene, polyethylene/polyethylene terephalate and co-polyethylene terephalate/polyethylene terephalate and having a first average denier, and about 40 weight percent of a polyester second fiber having a average second denier, wherein said first denier is 1 or less and is at least 3 denier less than said second denier, said second denier is between 4 and 15, and wherein said material has a basis weight between 30 and 200 gsm.

18. A surge material for personal care products comprising a between 40 and 60 weight percent of a first fiber having a first average denier and between 60 and 40 weight percent of a second fiber having a second average denier, wherein said first denier is 1 or less and is at least 3 denier less than said second denier, said second denier is between 4 and 15, and wherein said material has a basis weight between 30 and 200 gsm.

19. The nonwoven material of claim 18 wherein said first denier fiber is a bicomponent fiber.

20. The nonwoven material of claim 18 wherein said second denier fiber is made from a polyester.

* * * * *